United States Patent
Neal et al.

(10) Patent No.: US 9,474,686 B2
(45) Date of Patent: Oct. 25, 2016

(54) PACKAGE FOR SURGICAL IMPLANTS AND INSTRUMENTS

(75) Inventors: Kevin Neal, Tonbridge (GB); Thomas Stacey, Surbiton (GB)

(73) Assignee: FINSBURY (DEVELOPMENT) LIMITED (GB)

( * ) Notice: Subject to any disclaimer, the term of this patent is extended or adjusted under 35 U.S.C. 154(b) by 15 days.

(21) Appl. No.: 14/117,143

(22) PCT Filed: Apr. 18, 2012

(86) PCT No.: PCT/GB2012/050851
§ 371 (c)(1),
(2), (4) Date: May 22, 2014

(87) PCT Pub. No.: WO2012/153092
PCT Pub. Date: Nov. 15, 2012

(65) Prior Publication Data
US 2014/0299498 A1 Oct. 9, 2014

(30) Foreign Application Priority Data

May 12, 2011 (GB) .................................. 1107932.4
May 18, 2011 (GB) .................................. 1108267.4

(51) Int. Cl.
*A61J 1/00* (2006.01)
*A61F 2/00* (2006.01)
*A61F 2/34* (2006.01)

(52) U.S. Cl.
CPC ................ *A61J 1/00* (2013.01); *A61F 2/0095* (2013.01); *A61F 2/34* (2013.01)

(58) Field of Classification Search
CPC .... A01N 1/0263; A01N 1/02; A61F 2/0095; A61B 19/026; A61J 1/00; B65D 43/02; B65D 43/161
See application file for complete search history.

(56) References Cited

U.S. PATENT DOCUMENTS

| 3,013,656 A | 12/1961 | Murphy, Jr. |
| 3,855,638 A | 12/1974 | Pilliar |
| 4,697,703 A | 10/1987 | Will |

(Continued)

FOREIGN PATENT DOCUMENTS

| EP | 133393 A1 | 2/1985 |
| EP | 1205165 A1 | 5/2002 |
| WO | WO 0124730 A1 | 4/2001 |

OTHER PUBLICATIONS

PCT International Search Report and Written Opinion PCT/GB2012/050851 dated Jul. 17, 2012.

(Continued)

*Primary Examiner* — Andrew Perreault

(57) ABSTRACT

A package and method of packaging a surgical implant or surgical instrument are described. The package comprises a container and a holder having a recess arranged to receive a portion of a surgical implant or instrument, or a component coupled to the surgical implant or instrument. The holder is arranged to be at least partially received within the container. The holder has a first configuration in which the mouth of the recess is arranged to partially surround a portion of an implant or instrument, or a component coupled to the surgical implant or instrument, such that the recess grips the implant or instrument in position spaced apart from the container when the holder is at least partially received in the container. The holder also has a second configuration in which the mouth of the recess opens to release the implant or instrument.

14 Claims, 3 Drawing Sheets

(56) References Cited

U.S. PATENT DOCUMENTS

| | | |
|---|---|---|
| 4,750,619 A | 6/1988 | Cohen |
| 5,148,920 A | 9/1992 | Walker |
| 5,720,391 A | 2/1998 | Dohm |
| 5,868,253 A | 2/1999 | Krueger |
| 6,880,706 B2 * | 4/2005 | Braconnot et al. ............ 206/583 |
| 8,240,477 B2 * | 8/2012 | Lightner et al. .............. 206/583 |
| 2003/0214139 A1 | 11/2003 | Nigam |
| 2006/0058885 A1 | 3/2006 | Wozencroft |
| 2010/0140124 A1 | 6/2010 | Hafner |

OTHER PUBLICATIONS

UK Search Report GB1107932.4 dated Aug. 31, 2011.

* cited by examiner

US 9,474,686 B2

PACKAGE FOR SURGICAL IMPLANTS AND INSTRUMENTS

CROSS REFERENCE TO RELATED APPLICATION

This application is a National Stage 35 U.S.C. 371 of International Patent Application PCT/GB2012/050851 filed Apr. 18, 2012.

BACKGROUND OF THE INVENTION

The present invention relates to packaging for surgical implants and medical equipment. The present invention also relates to a method of packaging surgical implants and medical equipment.

It is well known to repair damage to bone through the use of surgical implants to replace part or all of the natural bone. For example, surgical reconstruction of a hip joint may require a femoral implant to be implanted at the end of the femur and an acetabular cup implant positioned within a reamed acetabular cavity or the natural acetabulum to receive the prosthetic bearing head.

It is known to provide a coating, which promotes osseointegration, to a surface of an implant that contacts the bone. Osseointegration is the direct structural and functional connection between living bone and the surface of an implant. Osseointegration may result from bioactive retention whereby the implant is coated with a bioactive material which stimulates bone formation leading to a chemical bond in which the implant is ankylosed with the bone. A suitable bioactive coating material is hydroxyapatite (HA, also known as hydroxylapatite). Hydroxyapatite is a naturally occurring mineral font of calcium apatite which forms up to seventy percent of natural bone. A hydroxyapatite coating stimulates bone formation.

Osseointegration may also result from mechanical retention whereby bone ingrowth into surface features of a prosthesis, secures the prosthesis to the bone. A suitable coating comprises a porous layer on a metallic substrate such that bone ingrowth into the pores forms a firm bond between the prosthesis and the bone. There is no chemical retention of the prosthesis and the retention is dependent upon the surface area of the prosthesis. The porous coating may consist of a plurality of small discrete particles of a metallic material bonded together at their points of contact to define a plurality of connected interstitial pores in the coating. Such a coating material, and a method of forming the coating, is described in U.S. Pat. No. 3,855,638. Such a porous coating is commercially available from DePuy Orthopaedics, Inc under the name Porocoat.

Implant coatings may be relatively delicate and susceptible to damage during handling prior to implantation. It is desirable to try to limit the amount of damage by limiting contact with the implant prior to delivery to the surgeon in the operating theatre. It is common practice to provide surgical implants in packages which are sealed by the manufacturer and only opened within the operating theatre. This also ensures that the implant remains sterile.

One known approach to packaging implants is to seal the implant within a first bag, and then place the whole bag in a second sealed bag to provide two sterile barriers. However, this causes the implant to contact the packaging, which risks damage to coatings on the implant. Additionally, when opening the package there is a risk that the implant may be dropped. For double bagged implants it can be difficult to read part numbers or other information printed upon the implants, without opening the package and breaching sterility. Additionally, the packaging may be relatively weak and susceptible to accidental damage.

It is known to provide packaging for products in which a first layer defines recesses to receive the product sealed with a web of material such as a layer of paper, cardboard, aluminium foil or plastic such that the products are trapped between the two layers. Such a package is called a blister pack. The first layer is made from a web of material which can be shaped to form the recesses, usually a thermoformed plastic. The plastic may be a thermoplastic polymer such as polyethylene terephthalate (PET), and in particular PETG which is a clear thermoplastic that can be injection moulded and is commonly used in food packaging. A suitable material for the second layer is Tyvek® which is a tear resistant clear plastic film.

It is known to use blister packs to package implants, however unless additional structures are built into the blister packs then the implants can move around within the packaging risking damage to coatings. U.S. Pat. No. 3,013,656 discloses the use of blister packs, with an additional support layer of cardboard behind the first layer to package surgical instruments to ensure the instruments are sterile when delivered to a surgeon. The first layer comprises a flexible plastic layer for instance polystyrene or vinyl and defines recesses to receive breakable articles. Some of the recesses have mouths which are narrower than the maximum width of the instruments to be received. The mouths deform when the instrument is inserted or removed to securely hold the instrument in position.

U.S. Pat. No. 4,697,703 discloses a blister pack for holding a medical item, such as a surgical implant. An inner package is received within an outer package each of which is sealed with a film cover to provide two sterile barriers. The inner package further includes a lid and a pair of shaped inserts to fit within the inner package. The inserts define projections which extend into the centre of the inner package to cradle the medical item such that the medical item is not free to move within the inner package.

It is an object of embodiments of the present invention to obviate or mitigate one or more of the problems associated with the prior art, whether identified herein or elsewhere.

BRIEF SUMMARY OF THE INVENTION

According to a first aspect of the present invention there is provided a package comprising: a container; and a holder having a recess arranged to at least partially receive a portion of a surgical implant or instrument, or a component coupled to the surgical implant or instrument, the holder being arranged to be received within the container; wherein the holder has a first configuration in which the mouth of the recess is arranged to partially surround a portion of an implant or instrument, or a component coupled to the surgical implant or instrument, such that the recess grips the implant or instrument in position spaced apart from the container when the holder is at least partially received in the container, and a second configuration in which the mouth of the recess opens to release the implant or instrument.

An advantage of the present invention is that the packaging allows the implant or instrument to be securely held during transport such that surfaces of the implant which are susceptible to damage are spaced apart from the sides of the packaging. The container can be sealed to form at least one sterile barrier. Additionally, in certain embodiments of the present invention, the implant holder can be removed from the container while still holding the implant or instrument, which allows aseptic presentation to the surgeon. This also reduces the risk of dropping the implant or instrument while opening the package. The recess of the holder may be arranged to receive a standard size portion of an implant which is available in a range of shapes and sizes thereby allowing the package to be standardised across a range of implants. The package may be transparent allowing the ready identification of part numbers printed upon the implant.

The container may have at least one wall which defines a volume to receive the holder.

When in the first configuration the holder may define a substantially planar surface.

When the implant or instrument is received in the container the container may act upon the holder to hold the holder in the first configuration.

In the first configuration the mouth of the recess may be arranged to engage a first portion of an implant or instrument, or a component coupled to an implant or instrument, having a first width such that a second portion of the implant or instrument, or a component coupled to the implant or instrument, is received within the recess and is prevented from being withdrawn through the mouth of the recess.

The holder may comprise first and second portions arranged to pivot with respect to one another from the first configuration to the second configuration.

When the holder is received in the container, the two portions of the holder may be prevented structurally from pivoting with respect to one another.

The holder may be arranged to fold to change the holder between the first configuration and the second configuration.

The holder may comprise first and second portions connected together along a fold line, each portion of the holder defining a respective portion of the recess such that folding the holder along the fold line moves the recess portions apart to open the mouth of the recess.

The holder may comprise a wall portion arranged to bear against an internal wall of the container when the holder is received within the container to prevent the holder from folding to the second configuration.

The container may be arranged to support the implant holder.

The package may further comprise a second container arranged to receive the first container.

The second container may comprise a step portion and the first container may comprise a flange portion arranged to rest upon the second container step portion when the first container is received in the second container such that remote from the flange the first container is spaced apart from the second container.

The first container may comprise a step portion and the holder may comprise a flange portion arranged to rest upon the first container step portion when the holder is received in the second container, the first container step portion being further arranged to bear against an internal wall of the second container to limit relative movement between the first container and the second container.

The or each container and the holder may be formed from a thermoformed plastic.

The or each container may be sealed by applying a film of plastic across a flange surrounding an open mouth of the container to form a sterile barrier.

The film of plastic across the mouth of the first container may bear against the holder to limit relative movement between the implant holder and the first container.

According to a second aspect of the present invention there may be provided a method of packaging a surgical implant or a surgical instrument comprising: receiving a portion of a surgical implant or instrument, or a component coupled to the surgical implant or instrument, in a recess of an implant holder; and inserting the holder into a container; wherein the holder has a first configuration in which the mouth of the recess is arranged to partially surround a portion of an implant or instrument, or a component coupled to an implant or instrument, such that the recess grips the implant or instrument in position spaced apart from the container, and a second configuration in which the mouth of the recess opens to release the implant.

The method may further comprise sealing the container to form a sterile barrier.

BRIEF DESCRIPTION OF THE DRAWINGS

An embodiment of the present invention will now be described, by way of example only, with reference to the accompanying drawings, in which.

DETAILED DESCRIPTION OF THE INVENTION

An acetabular cup implant is inserted into a prepared cavity in a patient's pelvis or into the natural acetabulum. A range of sizes is normally provided to suit different patients. Metallic acetabular cups are often implanted by providing a friction fit within a closely matched cavity. Typically this is achieved by applying an impaction force to the cup to force the cup into the cavity. To ensure that the impaction force is carefully controlled it is generally necessary that the cup is securely gripped on the end of an insertion tool. It is undesirable to have to provide multiple insertion tools to grip cups of different sizes.

Figure 3:
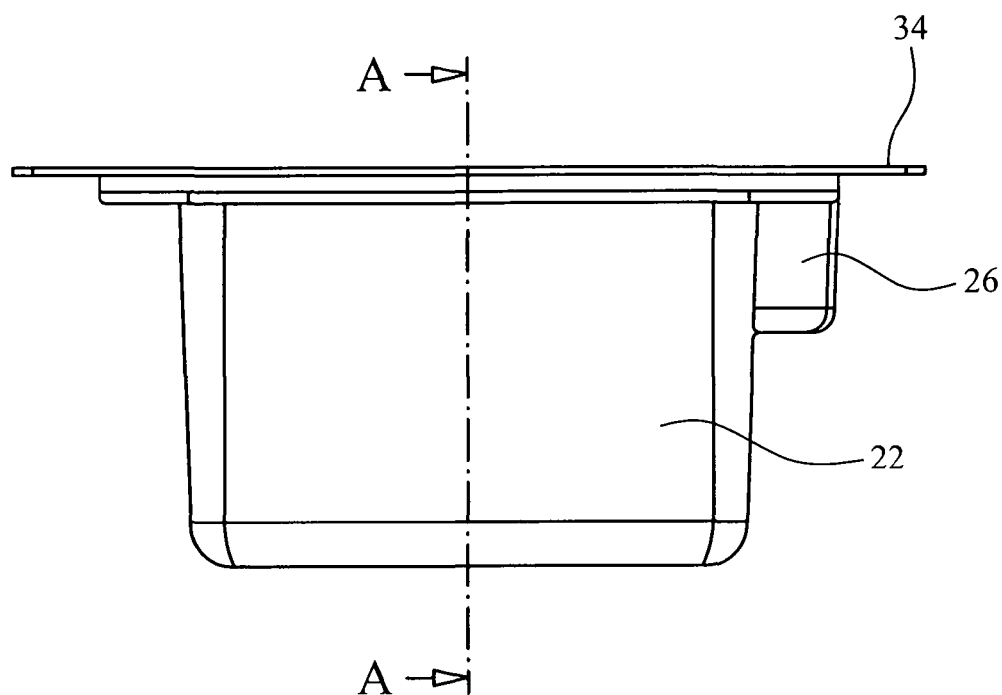
FIG. 3 is a side view of the implant package of FIG. 1.
Figure 4:
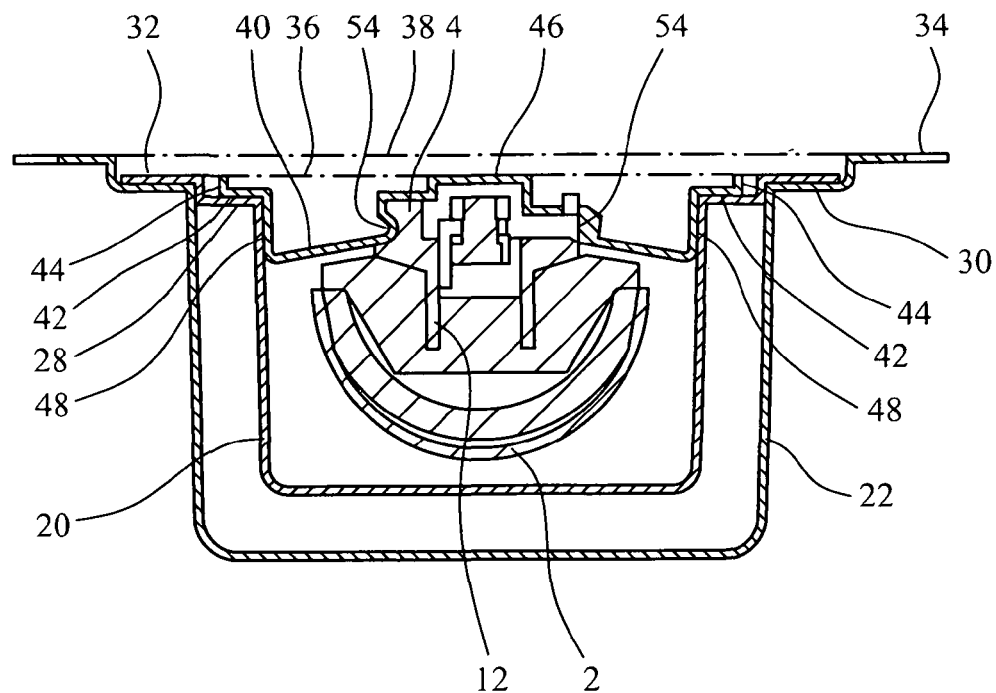
FIG. 4 is a cross sectional view of the implant package of FIG. 3 containing an implant along the line A:A shown in FIG. 3 in the direction of the arrows.
Figure 5:
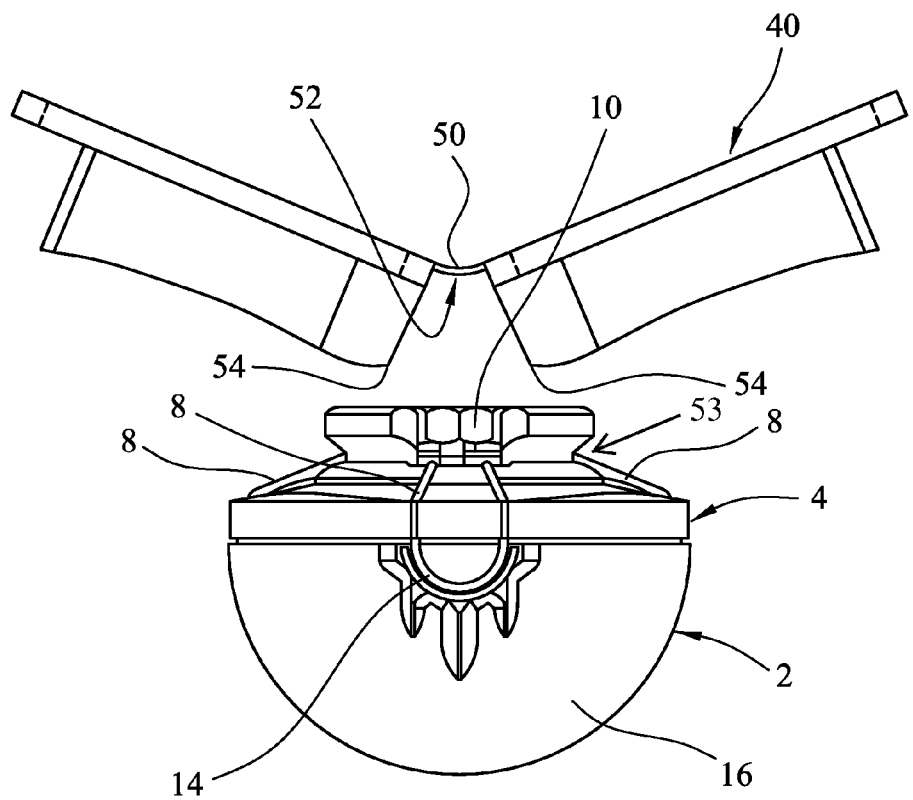
FIG. 5 is a side view of the cup holder part of the implant package of FIG. 1 showing how it couples to an implant.

US patent application publication number US-2006/0058885-A1 discloses a cap to couple to an acetabular cup for use during the insertion of the acetabular cup. The cap may be provided in a range of sizes to fit different acetabular cups which presenting a single interface to engage a single insertion tool. The cap may be made relatively small, and may be provided already coupled to the acetabular cup when the cup is delivered to a surgeon. After the cup is implanted the cap may be removed. An embodiment of the present invention relates to a surgical implant package arranged to package an acetabular cup and a cap generally similar to that disclosed in US patent application publication number US-2006/0058885-A1. FIGS. 3 to 5 illustrate an acetabular cup 2 and a cap 4 in combination with a surgical implant package according to the present invention. The cap 4 comprises an impaction plate 6, at least one cable loop 8 for connecting the impaction plate 6 to the cup 2, a clamp 10 for attaching the cable to the impaction plate 6 and a cutter 12 for severing the at least one cable loop 8 to release the cap 4 from the cup 2. The or each cable loop 8 connects to the cup 2 by passing around a lug 14 formed in the outer surface of the cup 2. An insertion tool (not illustrated) is arranged to couple to the cap 4 to transfer an impaction force to the cup 2.

The acetabular cup 2 has a convex outer surface 16 which may be coated with a material to promote osseointegration. As discussed above, it is desirable to prevent the surface 16 from coming into contact with packaging material. The embodiment of the present invention illustrated in FIGS. 1 to 6 is arranged to grip the cap 4 which in turn is secured to the cup 2 so that the cup 2 is spaced apart from the walls of the package. Advantageously by gripping only the cap 4 a single implant package may be used regardless of the size of the cup 2.

Referring to FIGS. 1 to 4 these illustrate an assembled view, an exploded view a side view and a cross sectional view respectively of a surgical implant package in accordance with an embodiment of the present invention. The surgical implant package comprises two separate containers comprising an inner blister (or container or first container) 20 and an outer blister (or second container) 22. Each blister 20, 22 may be vacuum formed from a thermoplastic such as PETG as described above. Preferably the blisters are transparent to allow the implant 2 (the acetabular cup) to be clearly viewed and any identification marks read. It can be seen that each blister 20, 22 is generally a rectangular dished shape (the walls of which create a volume), though there is an enlarged portion 24, 26 at the corner of each blister 20, 22 to ensure that the inner blister 20 can only be inserted into the outer blister 22 in a single orientation and also to facilitate separating the blisters 20, 22. Each blister 20, 22 comprises, a step 28, 30 and an upper flange 32, 34. When the smaller inner blister 20 is received in the larger outer blister 22 the inner blister flange 32 rests upon the outer blister step 30 and the outer edge of the inner blister step 28 ensures that the inner blister 20 is centrally located within the outer blister 22, as can be seen in the cross section of FIG. 4. FIG. 4 shows that the wall of the inner blister 20 is spaced apart from the outer blister 22 except at the point of the inner blister step 28 and flange 32.

The inner and outer blisters 20, 22 are separately sealed by applying a film or web 36, 38 of plastic such as Tyvek® across the opening of each blister 20, 22 sealed to the flanges 32, 34 as shown by the dashed lines in FIG. 4. Each sealed blister 20, 22 forms an independent sterile barrier.

The implant package further comprises an implant holder 40 arranged to engage a cap 4 coupled to an acetabular cup 2. As noted above, the cap 4 may be standardised to fit any cup 2, or at least may have a standard upper profile such that only a single form of implant holder 40 is required. The size of the inner blister 20 is chosen such that for the largest possible cup 2 sufficient space remains surrounding the cup 2 to prevent contact between the coated convex surface 16 and the inner blister 20. The implant holder 40 comprises a flange 42 arranged to rest upon the step part 28 of the inner blister. A raised rim 44 surrounds at least part of the implant holder 40 and is arranged to contact the plastic seal 36 over the inner blister 20 such that the implant holder is held firm against inner blister step 28. Additionally a raised central portion 46 of the implant holder 40 bears against and is held in place by the plastic seal 36. Side walls 48 of the implant holder 40 ensure that the implant holder 40 is centrally located within the inner blister 20, and prevent the implant holder 40 from opening up, as described below.

Figure 6:
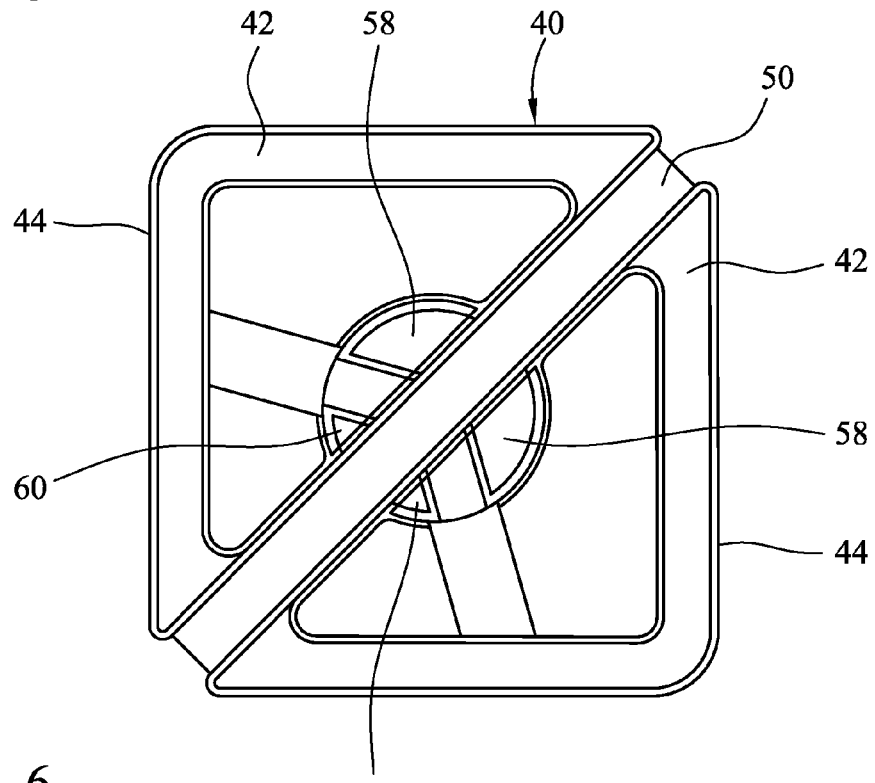
FIG. 6 is a top view of the cup holder of FIG. 5.

Referring now also to FIGS. 5 and 6, it can be seen particularly in the side view of FIG. 5 that the implant holder 40 comprises two halves connected by a web 50 arranged to fold. The underside of the implant holder 40 defines a recess 52 shaped to fit over the cap 4 coupled to the cup 2. With particular reference to FIG. 4, in a first configuration the cap 4 is partially received within the recess 52 such that the mouth 54 of the recess 52 closes around a narrowed portion (a first portion) 53 of the cap 4 to grip the cap 4. When the implant holder 40 is removed from the inner blister 20 as shown in FIG. 5 the implant holder 40 can be bent upwards into a second configuration along the web 50 such that the mouth 54 of the recess 52 opens to release the cap 4. When the implant holder 40 is received within the inner blister 20 the side walls 48 of the implant holder 40 bear against the inner blister 20 preventing the implant holder 40 from being bent to the second configuration, thereby preventing the implant 2 from being released.

Figure 1:
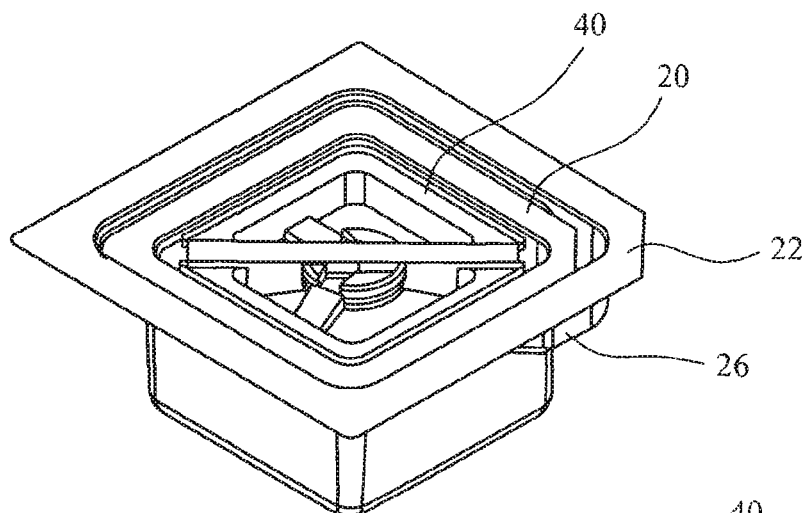
FIG. 1 is a perspective view of an implant package in accordance with an embodiment of the present invention.
Figure 2:
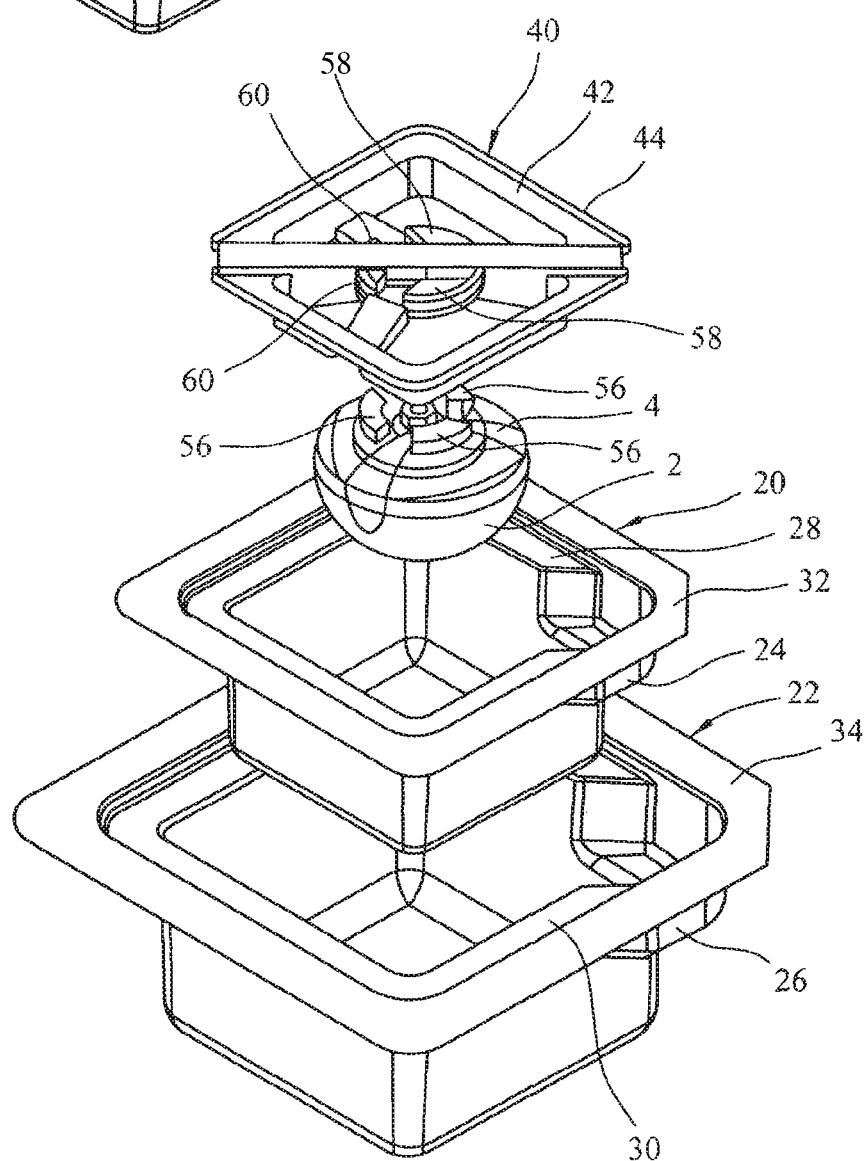
FIG. 2 is an exploded perspective view of the implant package of FIG. 1 containing an implant.

It can be seen in FIG. 2 that the portion (a second portion) 55 of the cap 4 gripped by the recess 52 comprises three spaced apart lobes 56. In each half of the implant holder 40 the recess comprises a corresponding lobe shape 58 and the third lobe is accommodated in two parts in half lobe shapes 60 as shown in the top view of the implant holder 40 of FIG. 6. The lobe shapes 58, 60 in the recess 52 prevent the implant 2 from rotating within the recess 52. It will be appreciated that in alternative embodiments of the present invention the shape of the recess will vary to match a portion of an implant or a component attached to an implant to be packaged.

While embodiments of the present invention described above relate to a surgical implant package arranged to contain a particular form of acetabular cup and insertion cap, the present invention is not limited to this. More generally, the present invention is applicable to packaging any fog in for surgical implant and the mouth of the recess of the implant holder may be adapted to partially surround and grip any suitable portion of the implant or a coupled disposable part. The shape of the blisters can be freely changed to accommodate implants of different sizes. Embodiments of the present invention could also be used for packaging surgical instruments where there is a feature that can be held in place by the holder. For instance, single use surgical instruments may be more delicate than multiple use instruments, in part because they are not required to withstand repeated sterilisation.

Consequently such instruments may benefit from being packaged in a manner that prevents contact between the instrument and the sides of the packaging.

Further modifications to, and advantages of, the present invention will be readily apparent to the appropriately skilled person from the teaching herein without departing from the scope of the appended claims.

The invention claimed is:

1. A package for a surgical implant, comprising:
a container; and
a holder having a recess arranged to receive a portion of the surgical implant or a component coupled to the surgical implant, the surgical implant or component coupled to the surgical implant having a cap, the holder being arranged to be at least partially received within the container, the recess include a plurality of lobe shapes adapted to engage the implant or component, wherein the recess only receives a portion of the cap;
wherein the holder has a first configuration in which a mouth of the recess is arranged to partially surround a portion of the implant or a component coupled to the surgical implant, such that the recess grips the implant in a position spaced apart from the container when the holder is at least partially received in the container, and a second configuration in which the mouth of the recess opens to release the implant wherein the holder includes a foldable web connecting two halves of the holder, such that the foldable web folds to move the holder between the first configuration and the second configuration; and wherein the foldable web extends diagonally across the holder.

2. The package of claim 1, wherein the container has at least one wall that defines a volume to receive the holder.

3. The package of claim 1, wherein, when the implant is received in the container, the container acts upon the holder to hold the holder in the first configuration.

4. The package of claim 1, wherein when in the first configuration the holder defines a substantially planar surface.

5. The package of claim 1, wherein when in the first configuration the mouth of the recess is arranged to engage a first portion of the implant or a component coupled to an implant, the mouth having a first width such that a second portion of the implant or a component coupled to the implant, is received within the recess and is prevented from being withdrawn through the mouth of the recess.

6. The package of claim 5, wherein when the holder is received in the container, the first portion and the second portion are prevented from pivoting with respect to one another.

7. The package of claim 1, wherein the holder comprises a wall portion arranged to bear against an internal wall of the container when the holder is received within the container to prevent the holder from folding to the second configuration.

8. The package of claim 1, wherein the container is arranged to support the holder.

9. The package of claim 1, wherein the container is a first container and the package further comprises a second container arranged to receive the first container.

10. The package of claim 9, wherein the second container comprises a step portion and the first container comprises a flange portion arranged to contact the second container step portion when the first container is received in the second container such that a portion other than the flange of the first container is spaced apart from the second container.

11. The package of claim 10, wherein the first container comprises a step portion and the holder comprises a flange portion arranged to contact the first container step portion when the holder is received in the second container, the first container step portion being further arranged to bear against an internal wall of the second container to limit relative movement between the first container and the second container.

12. The package of claim 1, wherein at least one of the container and the holder are formed from a thermoformed plastic.

13. The package of claim 1, wherein the container is sealed by applying a film of plastic across a flange surrounding an open mouth of the container to form a sterile barrier.

14. The package of claim 13, wherein the film of plastic across the mouth of the first container bears against the holder to limit relative movement between the implant holder and the first container.

* * * * *